(12) United States Patent
Jenkins et al.

(10) Patent No.: US 7,435,756 B2
(45) Date of Patent: Oct. 14, 2008

(54) PREPARATION AND DIABETIC USE OF GIBBERELLINS

(75) Inventors: Peter James Jenkins, East Prahran (AU); Minnie Wu, Mt Waverley (AU); David Shine Wu, Mt Waverley (AU)

(73) Assignee: Australian Biomedical Company Pty, Ltd., Mt. Waverley, Victoria (AU)

( * ) Notice: Subject to any disclaimer, the term of this patent is extended or adjusted under 35 U.S.C. 154(b) by 0 days.

(21) Appl. No.: 10/776,188

(22) Filed: Feb. 12, 2004

(65) Prior Publication Data
US 2004/0162248 A1 Aug. 19, 2004

Related U.S. Application Data

(63) Continuation of application No. PCT/AU02/01083, filed on Aug. 12, 2002.

(30) Foreign Application Priority Data

Aug. 31, 2001 (AU) .................... PR7380
Jul. 12, 2002 (AU) ............... 2002950182

(51) Int. Cl.
*A61K 31/21* (2006.01)
(52) U.S. Cl. .................. 514/510; 514/25; 514/33
(58) Field of Classification Search .......... 514/25, 514/33, 34, 468, 557, 569, 574, 577, 693, 514/700, 703, 705, 738, 739, 510
See application file for complete search history.

(56) References Cited

U.S. PATENT DOCUMENTS

| | | | | |
|---|---|---|---|---|
| 4,424,232 | A | | 1/1984 | Parkinson |
| 5,580,857 | A | * | 12/1996 | Oden ........................... 514/25 |
| 5,591,709 | A | * | 1/1997 | Lindenbaum ................... 514/4 |
| 6,121,317 | A | * | 9/2000 | Wu et al. ..................... 514/530 |
| 6,287,800 | B1 | * | 9/2001 | Gallazzo et al. ............... 435/65 |
| 6,312,663 | B1 | * | 11/2001 | Boykin, Jr. ................. 424/9.31 |

FOREIGN PATENT DOCUMENTS

| | | |
|---|---|---|
| EP | 0024951 B1 | 12/1983 |
| JP | 58-152499 | 10/1983 |
| JP | 02-165775 | 6/1990 |
| WO | WO 94/26240 | 11/1994 |
| WO | WO 96/20703 | 7/1996 |
| WO | WO 97/02032 | 1/1997 |

OTHER PUBLICATIONS

Davis, et al. *Aloe Vera and Gibberellin Anti-inflammatory Activity in Diabetes*, Journal of the American Podiatric Medical Association 79:1, 24-26 (Jan. 1989).
Int'l. Search Report in corresponding application PCT/AU02/01083, mailed Oct. 7, 2002.
Children's Medical Center at the University of Virginia, *Pediatric Pharmacotherapy*, 2:1-4 (1996).

Express Scripts, Inc., http://www.drugdigest.org/DD/PrintablePages/Comparisons/1,20038,8-21,00.html, printed on Mar. 8, 2005.
"Definition, Diagnosis and Classification of Diabetes Mellitus and its Complications," World Health Org., Dept. of Noncommunicable Disease Surveillance, Geneva 21-22 (1999).
Cardinal, et al., "Increased Susceptibility to Streptozotocin-Induced β-Cell Apoptosis and Delayed Autoimmune Diabetes in Alkylpurine-DNA-N-Glycosylase-Deficient Mice," *Molecular and Cellular Biology*, 21:5605-5613 (2001).
Ramasamy, et al., "Protein Kinase C and the Sub-Sensitivity and Sub-Reactivity of the Diabetic Rat Prostate Gland to Noradrenaline," *European Journal of Pharmacology*, 434:151-161 (2002).
Laposata, M., *SI Unit Conversion Guide*, Boston:NEJM Books, 81-83.
Murray, et al., "Effect of Meals and Posture on Concentration of Substances in Blood," *Harper's Biochemistry*, 24th Ed., p. 830-832.
*Dorland's Illustrated Medical Dictionary*, 25th Ed., Philadelphia:W. B. Saunders, 1673.
Sweetman, S.C. (Ed.), "Antidiabetics," *Martindale, The Complete Drug Reference*, 33rd Ed., London:Pharmaceutical Press, 315-316.
"Glucophage", *Glucolet Endcaps* 1561 (1996).
MIMS Annual, "Hypoglycaemic Agents," 612, 614-618, 620 (2003).
Chen et al., "Duration of Streptozotocin-Induced Diabetes Differentially Affects p38-Mitogen-Activated Protein Kinase (MAPK) Phosphorylation in Renal and Vascular Dysfunction" *Cardiovacular Diabetology* 4:3 (2005). Abstract.

(Continued)

*Primary Examiner*—Elli Peselev
(74) *Attorney, Agent, or Firm*—Finnegan, Henderson, Farabow, Garrett & Dunner

(57) ABSTRACT

The present invention relates to application of compounds of formula (1) (Gibberellins) and their derivatives for the preparation of a pharmaceutical composition or medicaments for the treatment of diabetes, its complications and associated conditions, including obesity, micro and macro vascular diseases, nephropathy, neuropathy, eye diseases, diabetic ulcerations and the like. The method results the normalization of serum glucose level and other physiological conditions

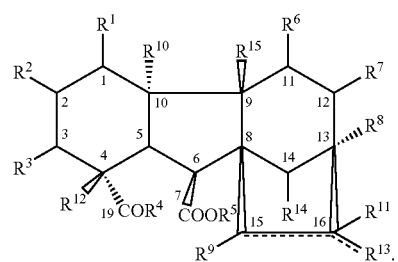

12 Claims, No Drawings

OTHER PUBLICATIONS

Heilbron, I.M. (Ed.), *Dictionary of Organic Compounds* 6th ed, London:Chapman & Hall, 2741-2747 (1996).

Rolandsson, et al., "Streptozotocin Induced Diabetes in Minipig: A Case Report of a Possible Model for Type 1 Diabetes" *Autoimmunity* 35:261-264 (2002). Abstract.

Loudon, M. *Organic Chemistry*, 3rd Ed. Redwood City, CA: Benjamin/Cummings Publishing Co., Inc., 131, 739 (1995).

March, J., *Advanced Organic Chemistry*, 4th Ed. New York: J. Wiley and Sons, 423 (1992).

Roberts, J. et al., *Basic Principles of Organic Chemistry*, New York: W. A. Benjamin Co., 148 (1964).

Loudon, *Organic Chemistry*, 3rd Ed. Redwood City, CA: Benjamin/Cummings Publishing Co., Inc., 1343-1348 (1995).

Sharp, *The Penguin Dictionary of Chemistry*, 5th Ed., Harmondsworth, England: Penguin Books, 193 (1983).

Shurtz-Swirski et al., "Involvement of Peripheral Polymorphonuclear Leukocytes in Oxidative Stress and Inflammation in Type 2 Diabetic Patients," *Diabetes Care*, 24:104-110 (2001).

"Antidiabetic Drugs," *The Year's Drug News, Therapeutic Targets* Barcelona: Prous Science, 351-360 (1995).

Uvarov et al., *A Dictionary of Science*, 4th Ed., Harmondsworth, England: Penguin Books, 169 (1971).

MacRury et al., "Changes in Phagocytic Function With Glycaemic Control in Diabetic Patients," *J. Clin. Pathol.* 42:1143-1147 (1989).

Benoit et al., "Insulin and Leptin as Adiposity Signals", *Recent Progress in Hormone Research*, 59:267-285, 2004.

DCCT/EDIC Research Group, "Retinopathy and Nephropathy in Patients with Type 1 Diabetes Four Years after a Trial of Intensive Therapy", *New England Jour. Med.*, 342:381-389, 2000.

MacRury et al., "Changes in Phagocytic Function With Glycaemic Control in Diabetic Patients," *J. Clin. Pathol.* 42:1143-1147, 1989.

Reichard et al., "The Effect of Long-Term Intensified Insulin Treatment on the Development of Microvascular Complications of Diabetes Mellitus", *New England Jour. Med.*, 329:304-309, 1993.

Webster's Collegiate Dictionary 855 (11th ed. 2003).

Mander, Twenty Years of Gibberellin Research, Nat. Prod. Rep., 20, pp. 49-69 (2003).

Reeve et al., An Assessment of Gibberellin Structure-Activity Relationships, J. of Exper. Bot., 25(85), pp. 431-445 (1974).

Yang et al., Effects of Gibberellins on Seed Germination of Phytochrome-Deficient Mutants of *Arabidopsis thaliana*, Plant Cell Physiol., 36(7), pp. 1205-1211 (1995).

Kren et al., *Current Med. Chem.*, 8:1313-38 (2001).

Sembdner et al., *Acta Universitatis Nicolai Copernici, Nauki Matematyczno-Przyrodnicze* 37:177-181 (1976).

Andreoli, Thomas E. et al., *Cecil Essentials of Medicine*, 4th Edition, W. B. Saunders Company, p. 536, (1997).

Loudon, G. Marc, *Organic Chemistry*, 4th Edition, Oxford University Press, pp. 1343-1348, (2002).

\* cited by examiner

PREPARATION AND DIABETIC USE OF GIBBERELLINS

RELATED APPLICATIONS

This application is a continuation of and/or claims priority under 35 U.S.C. § 119, 120 and/or 365 to PCT Patent Application No. PCT/AU02/01 083, filed Aug. 12, 2002, and Australian Patent Application No. 2002950182, filed Jul. 12, 2002 and Australian Provisional Patent Application No. PR 7380, filed Aug. 31, 2001.

The present invention relates to the use of compounds of formula (1) (Gibberellins) and their derivatives for the treatment of diabetes, its complications and associated conditions, including obesity, micro and macro vascular diseases, nephropathy, neuropathy, eye diseases, diabetic ulcerations and the like, and their use for the preparation of pharmaceutical compositions or medicaments for treatment of these conditions. The invention results the normalization of serum glucose level and other physiological conditions.

FIELD OF THE INVENTION

The present invention relates to the application of a group of compounds known as Gibberellins and their derivatives for the preparation of a pharmaceutical composition for the treatment of diabetes and related conditions, as well as a method for treating these and other conditions by administering Gibberellins and/or their pharmaceutically acceptable salts or esters including glycoside esters, active esters or lactones. Moreover, this invention relates to the manufacture and the use of a medicament for treating diabetes and related conditions thereof. Furthermore, the application of Gibberellins and their derivatives especially when administered orally, by injection, by transdermal patches, or by inhalation, can be used as a substitute for insulin and/or its fragment derivatives and/or IGFs (Insulin-like Growth Factors) treatment or as a choice of combination therapy with insulin, its fragment derivatives, IGF, growth factors or other pharmaceutically compatible anti-diabetic agents for the treatment of diabetes and related conditions.

BACKGROUND OF THE INVENTION

This invention relates to a novel application of Gibberellins in veterinary and human medicines. In particular the invention concerns pharmaceutical formulations containing Gibberellins and their use for the treatment of diabetes including type 1 and type 2 diabetes and their complications and associated conditions including obesity, micro and macro vascular diseases, nephropathy, neuropathy, eye diseases, diabetic ulcerations and the like.

Gibberellins are a series of naturally occurring compounds, which are known as plant growth regulators with wide application in the plant kingdom [1]. They have also been isolated from metabolites of some microorganisms, such as *Gibberella fujikuroi* [2]. Gibberellins, especially Gibberellic Acid (Gibberellin $A_3$), and its mixture with Gibberellin $A_4$ and/or Gibberellin $A_7$ which are commercially available, have been extensively applied in agriculture to increase the growth of some fruits (strawberries and grapes) and vegetables (tomatoes, cabbages and cauliflowers), also as food additive in the malting of barley [3].

[1]. J. MacMillian, et al. "Isolation and Structure of Gibberellin From Higher Plants". Adv. Chem. Ser 28, 18~24, (1961).

[2].
(a) P. J. Curtis et al. Chem. & Ind. (London) 1066, (1954).
(b) B. E. Cross, J. Chem. Soc. 4670, (1954).
(c) P. W. Brian et al, U.S. Pat. No. 2,842,051.
(d) C. T. Calam et al, U.S. Pat. No. 2,950,288.
(e) A. J. Birch et al, U.S. Pat. No. 2,977,285.

[3].
(a) M. Devlin, Plant Physiology, New York, Reinhold, (1966).
(b) P. W. Brian et al, Plant Physiol, 5,669 (1955).
(c) A. K Mehta et al, J. Hostic Sci 4, 167 (1975).
(d) R. J. Weavor, Adv. Chem. Ser 28, 89 (1961).
(e) F. G. Gustafson, Plant Physical 35, 521 (1960).
(f) Fed. Reg. 25, 2162 (1960).

Gibberellin $A_3$ and its mixture of Gibberellin $A_4$ and/or $A_7$ can be obtained by fermentation of microorganisms such as *Gibberella fujikuroi*. The crude compounds can be isolated and purified to afford a high purity crystalline product. The other derivatives of Gibberellin can be obtained by either semi-synthetic route from Gibberellin $A_3$ or total synthesis which have been well-documented [4].

[4].
(a) The Merck Index, 12, 4426, literatures cited herein.
(b) Furber M., et al., "New Synthesis Pathways From Gibberellins to Autheridiogens Isolated From the Fern Genus Anemia", J. of Org. Chem. vol 55, No. 15, 4860~4870 (1990).
(c) Mander L. N., et al., "C-18 hydroxylation of Gibberellins", J. C. S., Perkin Trans. 1 (17), 2893~2894 (2000).
(d) Pour M. et al., "Synthesis of 3,12-Dihydroxy-9,15-Cyclo Gibberellins", Tetrahedron 54(45), 13833~13850 (1998).
(e) Liu J. P. et al., "A General Protocol For the Hydroxylation of C-14 in Gibberellins Synthesis of 14-Beta-hydroxy-Gibberellin $A_1$ Methyl Ester", Tetrahedron 54(38), 11637~11650 (1998).
(f) Pour M, et al., "Synthetic and Structural Studies on Novel Gibberellins", Pure and Applied Chemistry 70(2), 351~354 (1998); "Synthesis of 12-Hydroxy-9,15-Cyclo-Gibberellins", Tetrahedron Letters, 39(14), 1991~1994 (1998); Australian J. of Chemistry 50(4), 289~299 (1997).
(g) King G. R. et al., "A New and Efficient Strategy for the Total Synthesis of Polycyclic Diterpenoids—The Preparation of Gibberellins (+/−)-$GA_{103}$ and (+/−)-$GA_{73}$", J. Am. Chem. Soc. 119(16), 3828~3829 (1997).
(h) Mander L. N., "Synthesis of 12-Hydroxy-C-20-Giebberellin from Gibberellin $A_3$", Tetrahedron 53(6), 2137~2162 (1997) and literatures cited herein.

Furthermore, the extraction and isolation of different Gibberellins from different plants, shoots, fruits and seeds have also been widely published [5].

[5].
(a) Pearce D. W., et al., Phytochemistry, 59(6), 679~687 (2002).
(b) Chang S. T., et al., Physiologia Plantarum, 112(3), 429~432 (2001).
(c) Nakayama M. et al., Phytochemistry, 57(5), 749~758 (2001); 48(4), 587~593 (1998).
(d) Blake P. S., et al., Phytochemistry, 55(8), 887~890 (2000); 53(4), 519~528 (2000).
(e) Koshioka M., et al., J. of the Japanese Society for Horticultural Science, 68(6), 1158~1160 (1999); 67(6), 866~871 (1998).
(f) Mander L. N. et al., Phytochemistry, 49(8), 2195~2206 (1998); 49(6), 1509~1515(1998).
(g) Wynne G. et al., Phytochemistry, 49(7), 1837~1840 (1998).

Gibberellins have previously been used for anti-inflammation, treatment of prostatitis and psoriasis, treatment of tumor, and for ulcer and wound healing [6].

[6].
(a) U.S. Pat. No. 4,424,232 January 1984 Parkinson
(b) French 2597339 October 1987
(c) U.S. Pat. No. 5,487,899 January 1996 Davis
(d) U.S. Pat. No. 5,580,857 December 1996 Oden
(e) AUS. 695054 November 1998 Wu
(f) U.S. Pat. No. 6,121,317 September 2000 Wu We have now found application of Gibberellin or its derivatives for the treatment of diabetes including type 1 and type 2 diabetes and their related conditions.

SUMMARY OF THE INVENTION

It has now been found that Gibberellins possess mammalian growth factor (such as IGF, EGF) like properties in our laboratory.

The experimental results (examples 3 and 4) suggested that Gibberellins, which are generated by plants and microbes, act as broad-spectrum binders binding to a range of growth factor receptors. They differ from the growth factors found in animals, each of which has a high affinity for a specific receptor. This is the result of evolution. The biological systems of plants and microbes produce biological substances acting on a broader (less specific) base than that of the more complex life forms such as animals.

Since Gibberellins are smaller molecules than growth factors, the binding of Gibberellins on the growth factor receptors is probably weaker. In the presence of low level of growth factors, Gibberellins bind to vacant growth factor receptors to stimulate cell growth and other functions. Under this condition, Gibberellins perform the functions of the growth factors. In the presence of normal level of growth factors, the growth factors bind to their receptors more readily due to their higher affinity for those receptor sites. The physical bulkiness of these growth factors leaves no room or very little room at the receptor sites for which Gibberellins can bind. This results in Gibberellins being ineffective when growth factors with sufficient binding affinity are present in sufficient quantities. This mechanism provides a very good profile for Gibberellins acting as a substitute or sensitizer for growth factors including IGF since the presence of excess Gibberellins will not interfere with the normal functions of these growth factors.

Diabetes mellitus is a chronic disorder manifested by hyperglycemia and altered lipid and protein metabolism. According to the American Diabetes Association, more than 13 million people in the U.S. suffer from diabetes, and each year some 650,000 new cases are identified. The introduction of insulin and of sulfonyl ureas represented important landmarks in the treatment of diabetes mellitus. Insulin like growth factor-1 (IGF-1), a molecule with structure homology to insulin, has its own specific receptor, the type-1 IGF receptor, through which it elicits a variety of metabolic effects that are similar to insulin. The discovery of the active region of human growth factor responsible for the insulin like actions of the molecule has led to the development of new anti-diabetic peptide agents. In addition, growth factors are polypeptides that regulate the replication, differentiation and metabolic homeostasis cells. They increase the growth and/or survival of neurons. In pre-clinical testing for the treatment of various neurological disorders including diabetic neuropathies, IGF-2 increased the rate of nerve regeneration. Furthermore, elevated intracellular concentrations of c-AMP potentiate glucose-dependent insulin secretion from pancreatic β-cells. Gibberellins have been found to increase the activity of adenylate and gryanylate cyclase, so that the intracellular concentrations of c-AMP and c-GMP may be increased by the administration of Gibberellins to potentiate in turn glucose-dependent insulin secretions from pancreatic β-cells. Gibberellins may thus be seen to have application in the treatment of diabetes.

The animal experiment results (examples 5 & 6) showed diabetic rats treated with 5 mg/kg of Gibberellin $A_3$ or a mixture of $A_3$ and $A_4$ or $A_7$ returned their serum glucose level to the normal, as well as their body weights. It indicated that Gibberellins may be effective in the treatment of diabetes.

The toxicity to mammals of Gibberellin $A_3$ is extremely low. The acute oral $LD_{50}$ for rats and mice is reported to be 6.3 g/kg [7a] and >15 g/kg [7] respectively. In 90-day feeding trials, the no effect level for rats and dogs was >1 g/kg/day [7b]. It is non-irritating to skin and eyes [7b]. No indication has been found of carcinogenicity [7c]. Classifications: WHO Toxicity Class Table 5 (least hazardous class product, unlikely to present acute hazard in normal use); EPA Toxcity class III (second least hazardous classification).

[7].
(a) NTP Chemical Repository, http://ntpserver.niehs.nih.gov/htdocs/CHEM_H&S/NTP_CHEM7/Radian77-06-5.html
(b) The Agrochemicals Handbook, Royal Society of Chemistry, August, 1991.
(c) Gold L. S., Slone T. H., Ames B. N. (2001), Pesticide Residues in Food and Cancer Risk: A Critical Analysis, Publications from the Carcinogenic Potency Project, in Handbook of Pesticide Toxicity, Second Edition, (R. Krieger, ed.), Academic Press.

Thus one aspect of this invention relates to use of compounds of Formula (1) (Gibberellins) or their derivatives for the treatment of diabetes and its complications and associated conditions including obesity, micro- and macro-vascular diseases, nephropathy, neuropathy, eye diseases, diabetic ulcerations and the like. In another aspect of the invention, there is provided a pharmaceutical formulation for the treatment of diabetes and related conditions including obesity, micro- and macro-vascular diseases, nephropathy, neuropathy, eye diseases, diabetic ulcerations and the like, said pharmaceutical formulation including Gibberellins, and/or their pharmaceutically acceptable salts or esters.

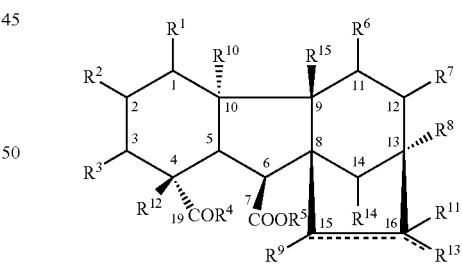

Gibberellins have the following formula:

Formula (1)

wherein
$R^1$ is H or a group —O—$R^{20}$, where $R^{20}$ is H, a glycosylic ether group (glycoside ether), $C_{1\sim 6}$ alkyl group, or $R^1$ together with $R^2$ or $R^{10}$ forms a bond ($C_1$-$C_2$ or $C_1$-$C_{10}$ double bond, respectively);

$R^2$ is H or a group —O—$R^{21}$, where $R^{21}$ is H, a glycosylic ether group (glycoside ether), or together with $R^4$ forms a bond (lactone) or $R^2$ together with $R^1$ or $R^3$ forms a bond ($C_1$-$C_2$ or $C_2$-$C_3$ double bond, respectively);

$R^3$ is H, =O, or —O—$R^{22}$, where $R^{22}$ is H or a glycosylic ether group (glycoside ether), or $R^3$ together with $R^2$ forms a bond ($C_2$-$C_3$ double bond);

$R^4$ is OH, or —$OR^{23}$, where $R^{23}$ is unsubstituted or substituted $C_{1\sim20}$ alkyl, allyl, aryl, arylalkyl, amidine, —$NR^{24}R^{25}$ or an unsaturated or saturated ring containing one or more hetero-atoms selected from the group consisting of nitrogen, oxygen and sulfur; $R^{24}$ and $R^{25}$ may or may not be the same, are hydrogen, or $C_{1\sim20}$ alkyl, allyl, aryl, arylalkyl or an unsaturated or saturated ring containing one or more hetero-atoms selected from the group consisting of nitrogen, oxygen and sulphur; or $R^4$ together with $R^{21}$ or $R^{28}$ forms a bond (lactone);

$R^5$ is H or a glycosylic ester (glycoside ester) group, or unsubstituted or substituted (e.g. halogenated) $C_{1\sim20}$ alkyl esters, allyl esters, aryl esters, arylalkyl esters, active esters (such as phenacyl ester, pivaloyl ester);

$R^6$ is H or OH or together with $R^7$ forms a bond ($C_{11}$-$C_{12}$ double bond);

$R^7$ is H, =O, or —$OR^{26}$, where $R^{26}$ is H or a glycosylic ether group (glycoside ether) or $R^7$ together with $R^6$ forms a bond ($C_{11}$-$C_{12}$ double bond);

$R^8$ is H, hydroxyl, mercaptan, or halogen (e.g. F, Cl), amino, azido, $NR^{24}R^{25}$, unsubstituted or substituted (e.g. halogenated) $C_{1\sim20}$ alkyl, allyl, aryl, or arylalkyl, or —$OR^{27}$, where $R^{27}$ is a glycosylic ether group (glycoside ether);

$R^9$ is H or OH, or together with $R^{15}$ forms a bond ($C_9$-$C_{15}$ bond);

$R^{10}$ is H, $CH_3$, CHO, COOH, or a glycosylic ester (glycoside ester) of said COOH, $CH_2O$—$R^{28}$ or —$OR^{28}$, where $R^{28}$ is H or together with $R^4$ forms a bond (lactone) or $R^{10}$ together with $R^1$ forms a bond ($C_1$-$C_{10}$ double bond);

$R^{11}$ is H, or OH or is absent;

$R^{12}$ is $CH_3$, $CH_2OH$, COOH or a glycosylic ester (glycoside ester) of said COOH;

$R^{13}$ is methylene, or a divalent hetero-atom, or $NR^{29}$, where $R^{29}$ is $NHR^{30}$ or $OR^{30}$ where $R^{30}$ is H, or $C_{1\sim20}$ alkyl, aryl, alkylaryl; and a double bond is present between $C_{16}$ and $R^{13}$ when $R^{11}$ is absent; or $R^{13}$ is H, OH, $CH_3$ CHO, $CH_2X$, where X is halogen (e.g. F, Cl); $CHNR^{29}$ where $R^{29}$ is $NHR^{30}$ or $OR^{30}$ where $R^{30}$ is H, or $C_{1\sim20}$ alkyl, aryl, alkylaryl when $R^{11}$ is H or OH; with the proviso that where $R^{11}$ is OH, $R^{13}$ is not OH $R^{14}$ is H or OH;

$R^{15}$ is H, or together with $R^9$ forms a bond ($C_9$-$C_{15}$ bond);

Pharmaceutically acceptable derivatives, including lactones, glycosides, esters, active esters, and salts of compounds of Formula (1), include alkali metal salts (e.g. $N^+$, $K^+$), alkaline earth metal salts (e.g. $Ca^{2+}$, $Mg^{2+}$), metal salts (e.g. $Zn^{2+}$, $Al^{3+}$), and salts of ammonium, organic bases thereof such as lidocaine, or $NR^{16}R^{17}R^{18}R^{19}$ where $R^{16}$, $R^{17}$, $R^{18}$, $R^{19}$, which may be the same or not the same, are hydrogen, $C_{1-20}$ alkyl, alkanoyl, aryl.

The dotted line together with the solid line indicate that a double bond may be situated between two of the three carbon atoms connected by the dotted and solid lines; with the proviso that a double bond is not present if $R^{11}$ is an OH group.

Since Formula (1) complies with normal valence rules, this leads to the further provisos as follows:

$R^1$ and $R^2$ cannot form a bond if $R^{10}$ and $R^1$ and/or $R^2$ and $R^3$ form a bond; $R^{10}$ and $R^1$ cannot form a bond if $R^{10}$ and $R^{23}$ form a bond; $R^2$ and $R^1$ or $R^2$ and $R^3$ cannot form a bond if $R^4$ and $R^{21}$ form a bond.

In the case of Gibberellin $A_3$, $R^1$ together with $R^2$ forms a bond ($C_1$-$C_2$ double bond); $R^3$ is β-OH, $R^4$ together with $R^{28}$ forms a bond (lactone); $R^5$, $R^6$, $R^7$, and $R^9$ are hydrogen, $R^8$ is OH, $R^{11}$ is absent; $R^{12}$ is methyl; $R^{13}$ is methylene, a double bond is present between $C_{16}$ and $R^{13}$; $R^{14}$ and $R^{15}$ are hydrogen.

The most readily available Gibberellins are Gibberellin $A_3$ and its mixture with Gibberellin $A_4$ and/or Gibberellin $A_7$ from the fermentation of *Gibberella fujikuroi*. Although the methods of isolation and purification of Gibberellins including solvent extraction, and chromatography have been published as mentioned in the background of the invention, a simple and efficient process for isolation and purification is still needed. In this invention a practical process for the large scale production of Gibberellin $A_3$ is provided, comprising the steps of incubating a Gibberellin-producing strain of microorganism in a fermentation broth until the concentration of Gibberellins reaches about 3000 μg/ml broth, followed by:

(a) adjusting the pH of the fermentation broth to pH 6.5 to 7.0 and filtering to obtain a filter cake of microorganism mycelium, and a filtrate;

(b) washing the filter cake with water and combining the washing with the filtrate to form an aqueous solution;

(c) concentrating the aqueous solution;

(d) mixing the aqueous solution with an organic solvent at a temperature of 5 to 10° C. and adjusting the pH of the mixture to less than 2.0;

(e) allowing the mixture to separate into an aqueous phase and a first organic phase and removing the first organic phase;

(f) re-extracting the aqueous phase from step (f) with organic solvent to obtain a second organic phase;

(g) combining the first and second organic phases and concentrating to form a concentrated organic solution;

(h) heating the concentrated organic solution at 60-70° C. for 3 to 4 hours with stirring, until the precipitation of solid matter ceases;

(i) cooling the concentrated organic solution to room temperature and filtering to obtain a precipitate;

(j) washing the precipitate in cold organic solvent and drying to obtain an off-white solid containing about 80% Gibberellin $A_3$, about 4% Gibberellin $A_4$ and about 4% Gibberellin $A_7$.

Optionally, the invention further comprises the steps of:

(k) dissolving the off-white solid in a mixture of 32.6% methanol, 2.2% water and 65.2% acetone to obtain a Gibberellin solution;

(l) diluting the Gibberellin solution with a 10:1 mixture of organic solvent and water;

(m) filtering the diluted Gibberellin solution and concentrating the filtrate by vacuum evaporation;

(n) heating the concentrate to a temperature of 60 to 80° C. for 2 to 3 hours with stirring, cooling to room temperature and filtering to obtain a solid crystalline precipitate; washing the precipitate with cold ethyl acetate and drying to obtain Gibberellin crystals at >95% purity.

Furthermore, processes for the preparation of Gibberellin salts and esters are disclosed. In particular, the invention includes a process for obtaining the sodium salt of Gibberellin, comprising the steps of:

(a) dissolving Gibberellin $A_3$ in methanol;

(b) adding the Gibberellin solution to an equimolar aqueous solution of $NaHCO_3$;

(c) evaporating the mixed solutions to dryness to obtain a solid residue;

(d) dissolving the residue in water and freeze drying to obtain Gibberellin $A_3$ sodium salt.

The invention further includes a process for obtaining the zinc salt of Gibberellin, comprising the further steps of dissolving Gibberellin $A_3$ sodium salt in water, passing the solution through a column loaded with a zinc ion-exchange resin, washing the column with water, collecting and combining the effluent and washings and removing the water to obtain Gibberellin $A_3$ zinc salt.

The invention further includes a process for obtaining the ethyl ester of Gibberellin, comprising the steps of:

(a) dissolving Gibberellin $A_3$ in a 50:1 ratio mixture of acetone to water;

(b) mixing the Gibberellin $A_3$ solution with equimolar amounts of triethylamine and ethyl chloroformate, and a one tenth molar amount of N-methyl morpholine, and stirring at −15° C. for 20 minutes;

(c) diluting the resultant mixture with anhydrous ethanol and stirring at room temperature;

(d) evaporating the diluted mixture to dryness and partitioning the residue between ethyl acetate and water in a 6:1 ratio;

(e) separating the ethyl acetate layer, washing with 2% HCl, followed by water, followed by 5% $NaHCO_3$, followed by water, and evaporating under reduced pressure to dryness to give Gibberellin $A_3$ ethyl ester.

References hereinafter to the compounds of formula (1) include the compounds of formula (1) and their pharmaceutically acceptable derivatives including salts, esters and lactones thereof.

Pharmaceutically acceptable compositions of the compounds of formula (1) may also be formed by combining them with one or more other active ingredients, for example insulin, insulin-like polypeptides, insulin fragment derivatives, IGFs, IGF fragments, growth factors, or other pharmaceutically compatible anti-diabetic agents for the treatment of diabetes and related conditions.

The compounds of formula (1) possess activity as insulin and insulin like agonists and/or sensitizers for the treatment of diabetes, its complications and associated conditions including obesity, micro and macro vascular diseases, nephropathy, neuropathy, eye diseases, diabetic ulcerations and the like. There is thus provided in a further aspect of the invention, the compounds of formula (1) for use as an active therapeutic agent in the treatment of diabetes and related conditions.

In a further aspect of the invention there is provided a method of manufacturing a pharmaceutical composition, comprising combining a compound of formula (1) and/or its derivatives with a pharmaceutically acceptable carrier.

In a further aspect of the invention, there is provided a method for the treatment of diabetes and related conditions in animals including humans comprising administering an effective amount of the compounds of formula (1).

There is also provided in a further aspect of the invention, the use of the compounds of formula (1) for the manufacture of a pharmaceutical composition for the treatment of diabetes and related conditions.

The amount of the compounds of formula (1) required for use in the treatment of diabetes and related conditions will vary with the rate of administration, the nature of the condition being treated and the age and condition of the animal including human patients and will ultimately be at the discretion of the attendant veterinarian or medical doctor.

In general a suitable dose will be in the range of from about 0.1 µg to 100mg/kg of body weight per day, preferably in the range of 50 µg to 20 mg/kg/day.

Treatment is preferably commenced after or at the time diabetes occurs and continues when it is needed. It is also possible to use the compounds of formula (1) as a prevention treatment.

Suitable treatment is given 1~4 times daily, and continued when it is needed. Alternatively, in the case of using a time release formulation, the treatment may be given once every 2 days to 1 week.

The desired dose may be presented in a single dose or as divided doses administered at appropriate intervals, for example as two, three, four or more sub-doses per day.

The compounds of formula (1) are conveniently administered in unit dosage form for example containing 0.1 to 500 mg of active ingredient per unit dosage form. While it is possible that, for use in therapy, the compounds of formula (1) will be administered as the raw chemical, it is preferable to present the active ingredient as a pharmaceutical formulation.

The invention thus further provides a pharmaceutical formulation including the compounds of formula (1) or a pharmaceutically acceptable derivative thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, intradermal, sub-cutaneous and intravenous) administration or in a form suitable for administration to the gastrointestinal tract, or in a form suitable for administration to the respiratory tract (including the nasal passages) for example by inhalation or insufflation or for intradermal or sub-cutaneous implantation or for transdermal patch. The formulations may, where appropriate, be conveniently presented in discrete dosage units and may be prepared by any of the methods known in the art of pharmacy. All methods include the step of bringing into association the active compound with liquid carriers or finely divided solid carriers or both and then, if necessary, shaping the product into the desired formulation.

Pharmaceutical formulations suitable for oral administration may be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds of formula (1) may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis the compounds of formula (1) may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening, or colouring agents.

For topical administration in the mouth, the compounds of formula (1) may be formulated as lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

For vaginal administration the formulations may be presented as pessaries, tampons, creams, gels, pastes, foams or sprays containing in addition to the active ingredient such carriers as are known in the art to be appropriate.

For rectal administration, unit dose suppositories wherein the carrier is a solid are preferred. Suitable carriers include cocoa butter and other materials commonly used in the art, and the suppositories may be conveniently formed by admixture of the active compound with the softened or melted carrier(s) followed by chilling and shaping in moulds.

For administration to the respiratory tract (including intranasal administration) compounds of formula (1) may be administered by any of the methods and formulations employed in the art for administration to the respiratory tract.

Thus in general the compounds of formula (1) may be administered in the form of a solution or a suspension or as a dry powder.

Solutions and suspensions will preferably be aqueous for example prepared from water alone (for example sterile or pyrogen-free water) or water and a physiologically acceptable co-solvent (for example ethanol, propylene glycol, and polyethylene glycols such as PEG 400).

Such solutions or suspensions may additionally contain other excipients for example preservatives (such as benzalkonium chloride), solubilising agents/surfactants such as polysorbates (e.g. Tween 80, Span 80, benzalkonium chloride), buffers, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multi-dose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomizing spray pump.

An aerosol formulation may also be used for the respiratory tract administration, in which the compounds of formula (1) are provided in a pressurized pack with a suitable propellant such as a chlorofluorocarbon (CFC) for example dichlorodifluoromethane, trichlorofluoromethane or dichlorotetrafluoroethane, carbon dioxide or other suitable gas. The aerosol may conveniently also contain a surfactant such as lecithin. The dose of drug may be controlled by provision of a metered valve.

Alternatively the compounds of formula (1) may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronisation.

For administration to the gastrointestinal tract, the compounds of formula (1) or a pharmaceutically acceptable derivative may be administered by any of the methods and formulations employed in the art for administration to the gastrointestinal tract.

When desired, formulations adapted to give sustained release of the active ingredient may be employed.

The compounds of formula (1) may also be used in combination with other therapeutic agents, for example anti-diabetic agents such as insulin, IGF, or analgesics, anti-hypertensive agents, sedatives, hypnotics, lipid-lowering agents, anti-infective agents and so on. The invention thus provides in a further aspect a combination comprising the compounds of formula (1) or a pharmaceutically acceptable derivative thereof together with another therapeutically active agent.

The combinations mentioned above may conveniently be presented for use in the form of a pharmaceutical formulation and thus such formulations comprising a combination as defined above together with a pharmaceutically acceptable carrier therefore comprise a further aspect of the invention.

The individual components of such combinations may be administered either sequentially or simultaneously in separate or combined pharmaceutical formulations.

When the compounds of formula (1) are used with a second therapeutic agent active in treatment of diabetes and related conditions, the dose of each compound may either be the same as or differ from that employed when each compound is used alone. Appropriate doses will be readily appreciated by those skilled in the art.

The compounds of formula (1) and their pharmaceutically acceptable derivatives may be prepared by any methods known in the art for the preparation of compounds of analogous structure.

The present invention is further described by the following examples, which are for illustrative purpose only and should not be construed as a limitation of the invention.

Detailed Description

EXAMPLE 1

Fermentation, Isolation and Purification of Gibberellins (a) Fermentation: Gibberellin $A_3$, $A_4$ and $A_7$ producing strain *Gibberella fujikuroi* was inoculated and grown in a medium containing 100 g glucose, 100 g sucrose, 2.5 g $NH_4NO_3$, 0.25 g $KH_2PO_4$, 0.2 g $MgSO_4$, 0.01 g $FeSO_4 7H_2O$, 0.03 g $ZnSO_4 7H_2O$, 0.1 g KCl, 10 g peptone, 3 g $CaCO_3$, 1000 ml $H_2O$, at 28° C. for 3~4 days. It was then transferred into a production medium containing 1000 g glucose, 100 g peptone, 24 g $NH_4NO_3$, 100 g $KH_2PO_4$, 20 g $MgSO_4 7H_2O$, 20 g $FeSO_4 7H_2O$, 1.5 g $Na_2B_4O_7.10H_2O$, 8 g $CuSO_4 7H_2O$, 0.7 g $(NH_4)_6Mo_7O_{24} 4H_2O$, 20 liter $H_2O$, at pH 4.5 at 28° C. for 8~10 days. When the production of Gibberellins reached to peak (~3000 □g/ml broth), the fermentation was stopped.

(b) Isolation: The fermentation broth (18 liter) was adjusted to pH 6.5~7.0 with 10% NaOH, then filtered off. The filter-cake (mycelium) was washed with 4 L of $H_2O$. The filtrate and washings were combined and vacuum evaporated to a volume of 2 L. The concentrate was stirred at 5~10° C. with ethyl acetate (5 L) and adjusted to pH 1.5 with 6NHCl. Then two layers were separated. The lower aqueous layer was re-extracted with ethyl acetate (2 L). The organic extracts were combined, and washed with water (2 L), then evaporated to 400 ml. The concentrate was stirred and heated at 60~70° C. for 3~4 hours until no more precipitation occurred. After cooling to room temperature, the suspension was filtered. The solid was washed with cold ethyl acetate and dried to afford Gibberellin $A_3$ and $A_4/A_7$ mixture as an off-white solid (45 g). This mixture contains ~80% $A_3$, ~4% $A_4$ and ~4% $A_7$.

(c) Purification: 10 g of the mixture of Gibberellin $A_3$ and $A_4/A_7$, as mentioned above, was dissolved in a mixture of 15 ml methanol containing 1 ml $H_2O$, and 30 ml acetone. The solution was diluted with 100 ml ethyl acetate containing 10 ml of $H_2O$. The mixture was filtered. The filtrate was vacuum evaporated to a volume of about 80 ml. The mixture was stirred and heated at 60~80° C. for 2~3 hours, then cooled to room temperature. It was filtered off. The solid was washed with cold ethyl acetate and dried to afford Gibberellin $A_3$ at >95% purity as a white crystal (6.3 g). MS: 391 $(M-1+2Na)^+$ 369 $(M+23)^+$ 329 $(M+1-H_2O)^+$ Example 2

Preparation of Gibberellin $A_3$ Salts and Esters (a) Preparation of Gibberellin $A_3$ sodium salt: A solution of 346 mg (1 mmole) of Gibberellin $A_3$ was dissolved in 1.5 ml of methanol, was added to a solution of $NaHCO_3$ (84 mg, 1 mmole) in 2 ml $H_2O$. The whole mixture was evaporated under reduced pressure to dryness. The residue was then dissolved in water (2 ml) and freeze dried to afford Gibberellin $A_3$ sodium salt was a white solid at quantitative yield.

(b) Preparation of Gibberellin $A_3$ zinc salt: 100 mg of Gibberellin $A_3$ sodium salt was dissolved in 10 ml water, then passed through a column (20 ml) Dowex 50 Zinc ion form resin. The column was then washed with 30 ml $H_2O$. The effluent and washings were combined and vacuum evaporated to small volume, then freeze dried to afford Gibberellin $A_3$ zinc salt as a white solid at quantitative yield.

(c) Preparation of Gibberellin $A_3$ ethyl ester: 346 mg (1 mmole) of Gibberellin $A_3$ was dissolved in a mixture of acetone (10 ml) and water (0.2 ml). To the mixture at −20° C., triethylamine (100 mg, 1 mmole), N-methyl morpholine (10 mg, 0.1 mmole), ethyl chloroformate (108 mg, 1 mmole) were added. The mixture was stirred at −15° C. for 20 minutes, then diluted with anhydrous ethanol (10 ml). The mixture was stirred at room temperature overnight, then evaporated to dryness. The residue was then partitioned between ethyl acetate (30 ml) and water (5 ml). The organic layer was separated and washed successively with 2% HCl (5 ml), water (5 ml), 5% $NaHCO_3$ (5 ml×2), water (5 ml), then evaporated under reduced pressure to dryness to afford a colorless solid Gibberellin $A_3$ ethyl ester (319 mg, 85%) MS 375 $(M+1)^+$.

Example 3

(a) Effect of Gibberellin $A_3$ on cell growth compared to EGF in vitro.

Human skin cell culture experiments were conducted by using keratinocytes media. Each well was seeded with 1,500 cells. Incubation was carried out at 37° C. for a period of five days. The experiments are shown as follows:

| Experiment | Media | Results |
|---|---|---|
| 3.1 | Perfect keratinocyte medium (containing EGF) | Very good growth (cell division rate = 100) |
| 3.2 | Perfect keratinocyte medium (containing EGF) plus Gibberellin $A_3$ (5□ g/ml) | Very good growth (cell division rate = 100) |
| 3.3 | Keratinocyte medium containing no EGF | Poor growth |
| 3.4 | Keratinocyte medium containing no EGF, but containing Gibberellin $A_3$ (5□ g/ml) | Very good growth (cell division rate ≈ 100) |

Experiments 3.1 and 3.3 indicated that EGF (Epidermal Growth Factor) is essential for cell growth. Experiment 2 indicated that the presence of both EGF and Gibberellin $A_3$ had no additive effect on the rate of cell growth. Experiment 4 gave an indication that Gibberellin $A_3$ alone can stimulate cell growth as effectively as EGF.

(b) Effect of Gibberellin $A_3$ compared to IGF on cell culture growth using IGF-1 replace the EGF for the cell culture experiment, mentioned in (a). The results were similar to the results in (a).

Example 4

The effect of a mixture of Gibberellin $A_3$ with Gibberellins $A_4$ and/or $A_7$ was compared to that of IGF-1 on the cell growth in vitro. The results were similar to those in example 3(b).

Example 5

Effect of Gibberellin $A_3$ on Diabetic Rats

Methods:

Male Wistar rats (290 g~330 g) were weighed and lightly anaesthetized (4% halothane, 2:1 $O_2/N_2O$) so that blood glucose levels could be measured via a tail vein sample, using a Precision Q.I.D. glucometer. Diabetes was then induced by a single tail vein injection of streptozotocin (STZ, 60 mg/kg), which was dissolved immediately prior to use in citrate buffer (50 mM citric acid and 50 mM trisodium citrate; pH 4.5). An equivalent volume of citrate buffer was injected into age-matched control rats.

Rats were housed in groups of two during the experiment. Animal house temperature was maintained at 20° C. (±2° C.) with a 12 hour light/dark cycle, and rats were allowed free access to food and water.

Ethical approval for all experiments was obtained from the Pharmacology Animal Ethics Committee.

Drug Administration and Daily Monitoring Protocol:

Forty-eight hours after the administration of STZ (60 mg/kg), a blood glucose sample was taken and animals with blood glucose levels ≧16 mM were considered to be diabetic. Rats were then randomly divided into groups.

The slow-acting, Lente Monotard insulin was used and Gibberellin sodium salt was made up as required in distilled water immediately prior to use.

Blood glucose readings were obtained two hours or 5 hours after the administration of drug(s) every three days. The results are shown as follows:

| Group No. | Administered daily | Blood glucose level (mM) after day 20th 2 hours | Blood glucose level (mM) after day 20th 5 hours | Body weight change on the 30th day |
|---|---|---|---|---|
| 1 | Insulin 4 unit/rat (sub-cutaneous) | 4~5 | 3~5 | +8% |
| 2 | Insulin 2 unit/rat (sub-cutaneous.) | 15~18 | 14~16 | -8% |
| 3 | Gibberellin $A_3$ 5 mg/kg (sub-cutaneous) + 2 unit insulin/rat (sub-cutaneous) | 4~6 | N.A. | +10% |
| 4 | Gibberellin $A_3$ 5 mg/kg (intraperitoneal) + 2 unit insulin/rat (sub-cutaneous) | 4~5 | 4~6 | +12% |
| 5 | Gibberellin $A_3$ 5 mg/kg (oral) + 2 unit insulin/rat (sub-cutaneous.) | N.A. | 4~6 | +10% |

Example 6

Effect of Gibberellin $A_3$ and $A_4/A_7$ Mixture on Diabetic Rats

The protocol of this experiment is the same as that in Example 5 but Gibberellin $A_3$ and $A_4/A_7$ mixture was used instead of Gibberellin $A_3$. The results were no different from those in Example 5.

The invention claimed is:

1. A method of treatment for Type II diabetes and its complications and associated conditions comprising administering a compound selected from formula (1) (Gibberellins)

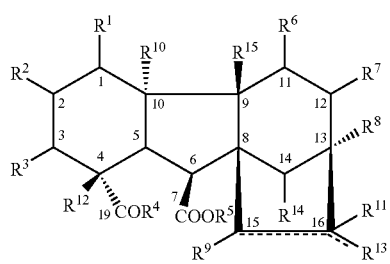

Formula (1)

wherein
$R^1$ is H or a group —O—$R^{20}$, where $R^{20}$ is H, or $R^1$ together with $R^2$ forms a bond ($C_1$-$C_2$ double bond);
$R^2$ is H or a group —O—$R^{21}$, where $R^{21}$ is H, or $R^2$ together with $R^1$ or $R^3$ forms a bond ($C_1$-$C_2$ or $C_2$-$C_3$ double bond, respectively);
$R_3$ is H, =O, or —O—$R^{22}$, where $R^{22}$ is H, or $R^3$ together with $R^2$ forms a bond ($C_2$-$C_3$ double bond);
$R^4$ together with $R^{28}$ forms a bond (lactone);
$R^5$ is H, or unsubstituted or substituted $C_{1\sim20}$ alkyl esters, allyl esters, active esters;
$R^6$ is H or OH or together with $R^7$ forms a bond ($C_{11}$-$C_{12}$ double bond);
$R^7$ is H or —$OR^{26}$, where $R^{26}$ is H or $R^7$ together with $R^6$ forms a bond ($C_{11}$-$C_{12}$ double bond);
$R^8$ is H or hydroxyl;
$R^9$ is H or OH;
$R^{10}$ —$OR^{28}$, where $R^{28}$ together with $R^4$ forms a bond (lactone);
$R^{11}$ is absent;
$R^{12}$ is $CH_3$;
$R^{13}$ is methylene;
$R^{14}$ is H;
$R^{15}$ is H;

and its pharmaceutically acceptable lactones, esters, active esters, salts and organic bases, in combination with other compatible therapeutic agents selected from the group consisting of analgesics, anti-hypertensive agents, sedatives, hypnotics, lipid-lowering agents, and anti-infective agents or combinations thereof, to a patient in need thereof.

2. A method of treatment for Type I or Type II diabetes and its complications and associated conditions comprising administering compounds selected from formula (1) (Gibberellins)

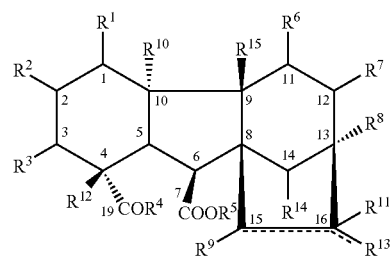

Formula (1)

wherein
$R^1$ is H or a group —O—$R^{20}$, where $R^{20}$ is H, or $R^1$ together with $R^2$ forms a bond ($C_1$-$C_2$ double bond);
$R^2$ is H or a group —O—$R^{21}$, where $R^{21}$ is H, or $R^2$ together with $R^1$ or $R^3$ forms a bond ($C_1$-$C_2$ or $C_2$-$C_3$ double bond, respectively);
$R^3$ is H, =O, or —O—$R^{22}$, where $R^{22}$ is H, or $R^3$ together with $R^2$ forms a bond ($C_2$-$C_3$ double bond);
$R^4$ together with $R^{28}$ forms a bond (lactone);
$R^5$ is H, or unsubstituted or substituted $C_{1\sim20}$ alkyl esters, allyl esters, active esters;
$R^6$ is H or OH or together with $R^7$ forms a bond ($C_{11}$-$C_{12}$ double bond);
$R^7$ is H or —$OR^{26}$, where $R^{26}$ is H or $R^7$ together with $R^6$ forms a bond ($C_{11}$-$C_{12}$ double bond);
$R^8$ is H or hydroxyl;
$R^9$ is H or OH;
$R^{10}$ is —$OR^{28}$, where $R^{28}$ together with $R^4$ forms a bond (lactone);
$R^{11}$ is absent;
$R^{12}$ is $CH_3$;
$R^{13}$ is methylene;

$R^{14}$ is H;
$R^{15}$ is H;
and their pharmaceutically acceptable lactones, esters, active esters, salts and organic bases, in combination with substances selected from the group consisting of insulin, its fragment derivatives, IGFs, and growth factors, or combinations thereof, to a patient in need thereof.

3. A method according to claim 2, wherein the Gibberellins are Gibberellin $A_3$.

4. A method according to claim 2, wherein the Gibberellins are a mixture of Gibberellin $A_3$ and Gibberellin $A_4$ and/or Gibberellin $A_7$.

5. A method of treatment for Type I or Type II diabetes and its complications and associated conditions comprising administering compounds selected from formula (1) (Gibberellins)

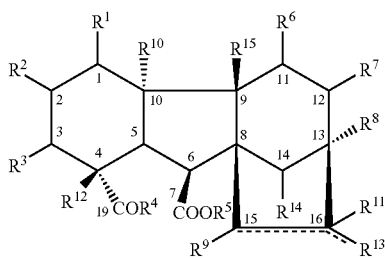

Formula (1)

wherein
$R^1$ is H or a group —O—$R^{20}$, where $R^{20}$ is H, or $R^1$ together with $R^2$ forms a bond ($C_1$-$C_2$ double bond);
$R^2$ is H or a group —O—$R^{21}$, where $R^{21}$ is H, or $R^2$ together with $R^1$ or $R^3$ forms a bond ($C_1$-$C_2$ or $C_2$-$C_3$ double bond, respectively);
$R^3$ is H, =O, or —O—$R^{22}$, where $R^{22}$ is H, or $R^3$ together with $R^2$ forms a bond ($C_2$-$C_3$ double bond);
$R^4$ together with $R^{28}$ forms a bond (lactone);
$R^5$ is H, or unsubstituted or substituted $C_{1\sim20}$ alkyl esters, allyl esters, active esters;
$R^6$ is H or OH or together with $R^7$ forms a bond ($C_{11}$-$C_{12}$ double bond);
$R^7$ is H or —$OR^{26}$, where $R^{26}$ is H or $R^7$ together with $R^6$ forms a bond ($C_{11}$-$C_{12}$ double bond);
$R^8$ is H or hydroxyl;
$R^9$ is H or OH;
$R^{10}$ is —$OR^{28}$, where $R^{28}$ together with $R^4$ forms a bond (lactone);
$R^{11}$ is absent;
$R^{12}$ is $CH_3$;
$R^{13}$ is methylene;
$R^{14}$ is H;
$R^{15}$ is H;
and its pharmaceutically acceptable lactones, esters, active esters, salts and organic bases, in combination with substances selected from the group consisting of insulin, its fragment derivatives, IGFs, and growth factors, or combinations thereof, along with other compatible therapeutic agents selected from the group consisting of analgesics, anti-hypertensive agents, sedatives, hypnotics, lipid-lowering agents, and anti-infective agents or combinations thereof, to a patient in need thereof.

6. The method according to claim 4, for the treatment of Type 1 diabetes and its associated conditions.

7. The method according to claim 4, for the treatment of Type 2 diabetes and its associated conditions.

8. The method according to claim 7, for the treatment of insulin resistant diabetes.

9. The method according to claim 4, wherein the diabetic related complications and associated conditions are chosen from obesity, micro and macro vascular diseases, nephropathy, neuropathy and eye diseases.

10. The method of claim 4, wherein the complications and associated conditions of diabetes are one or more of: obesity, micro and macro vascular diseases, nephropathy, neuropathy, eye diseases, and diabetic ulcerations.

11. The method of claim 4, wherein the pharmaceutically acceptable salts are selected from alkali metal salts, alkaline earth metal salts, metal, and salts of ammonium or salts of organic bases.

12. The method of claim 11, wherein the organic bases are lidocaine, or $NR^{16} R^{17} R^{18} R^{19}$, where $R^{16}$, $R^{17}$, $R^{18}$, $R^{19}$, which may be the same or not the same, are hydrogen, or substituted or unsubstituted $C_{1\sim20}$ alkyl, alkanol, or aryl groups.

* * * * *

UNITED STATES PATENT AND TRADEMARK OFFICE
CERTIFICATE OF CORRECTION

PATENT NO. : 7,435,756 B2
APPLICATION NO. : 10/776188
DATED : October 14, 2008
INVENTOR(S) : Peter James Jenkins et al.

It is certified that error appears in the above-identified patent and that said Letters Patent is hereby corrected as shown below:

In the Summary of the Invention, col. 5, line 53:

"thereof such as lidocaine, or $NR^{16}R^{17}R^{16}R^{19}$ where $R^{16}$, $R^{17}$,"

should read

--thereof such as lidocaine, or $NR^{16}R^{17}R^{18}R^{19}$ where $R^{16}$, $R^{17}$,--

In the Detailed Description, col. 11, line 9:

"(~3000 □g/ml broth), the fermentation was stopped."

should read

--(~3000 μg/ml broth), the fermentation was stopped.--

In the Detailed Description, col. 12, line 22:

"Gibberellin A3 (5 □g/ml)"

should read

--Gibberellin A3 (5 μg/ml)--

UNITED STATES PATENT AND TRADEMARK OFFICE
CERTIFICATE OF CORRECTION

PATENT NO. : 7,435,756 B2
APPLICATION NO. : 10/776188
DATED : October 14, 2008
INVENTOR(S) : Peter James Jenkins et al.

It is certified that error appears in the above-identified patent and that said Letters Patent is hereby corrected as shown below:

In the Detailed Description, col. 12, line 27:

"(5 □g/ml)"

should read

--(5 µg/ml)--

Signed and Sealed this

Third Day of March, 2009

JOHN DOLL
*Acting Director of the United States Patent and Trademark Office*